United States Patent [19]
Asai et al.

[11] 4,066,502
[45] Jan. 3, 1978

[54] METHOD OF PRODUCING CARBON SOURCE FOR FERMENTATION

[75] Inventors: Soichiro Asai, Tokyo; Tsutomu Matsuishi; Katsunobu Matsushita, both of Kawasaki; Shigeho Ikeda, Yokohama; Kaetsu Kobayashi; Hiromasa Maruyama, both of Tokyo, all of Japan

[73] Assignee: Ajinomoto Co., Inc., Tokyo, Japan

[21] Appl. No.: 678,116

[22] Filed: Apr. 19, 1976

[51] Int. Cl.² .................... C12D 13/06; C12B 3/04
[52] U.S. Cl. .............................. 195/47; 195/29; 195/102
[58] Field of Search ............ 195/47, 29, 31 F, 100, 195/102, 106; 127/41

[56] References Cited

U.S. PATENT DOCUMENTS

| | | | |
|---|---|---|---|
| 2,492,673 | 12/1949 | Woodward et al. | 195/36 R |
| 3,793,146 | 2/1974 | Ishii et al. | 195/37 |
| 3,812,010 | 5/1974 | Nitsch | 195/31 F |

Primary Examiner—Lionel M. Shapiro
Attorney, Agent, or Firm—Oblon, Fisher, Spivak, McClelland & Maier

[57] ABSTRACT

A hydrolyzate of molasses, containing both glucose and fructose, is mixed with calcium hydroxide, and a fructose addition precipitate is recovered. The residual liquor is neutralized, calcium ions are removed, and then the liquor is used as a carbon source for glutamic acid or lysine fermentation.

The present method may supply very inexpensive fructose to the market.

5 Claims, No Drawings

METHOD OF PRODUCING CARBON SOURCE FOR FERMENTATION

BACKGROUND OF THE INVENTION

1. Field of the Invention

This invention relates to a method of producing a novel carbon source for fermentation, and also to provide a very inexpensive source of fructose which is economically comparable to sucrose.

2. Description of the Prior Art

Fructose has a comfortable sweetness, and it is about 1.5 - 2 times as sweet as sucrose. There have been known many manufacturing processes for fructose, however, the manufacturing cost is too expensive and accordingly its market is restricted to such special uses as for foods for diabetics.

Sucrose is widely employed as a raw material for the production of fructose. However, it is difficult to treat the mother liquor after the fructose has been recovered. Many methods of treating the mother liquor have been investigated, for example, treating with glucose isomerase, but so far no economically satisfactory process has been developed.

It has been reported in U.S. Pat. No. 3,793,146 that fructose is recovered from a sucrose hydrolyzate in the form of an addition product with calcium chloride and the mother liquor is used as a main carbon source for fermentation of citric acid. However, the fructose produced by the method described in that U.S. patent is expensive because in the calcium chloride method, the sucrose must be pure. Furthermore, the kind of fermentation is limited because a large quantity of calcium ions and chloride ions remain in the mother liquor and inhibit the fermentation.

SUMMARY OF THE INVENTION

It has now been found that when fructose is recovered from a hydrolyzate of molasses in the form of an addition product of calcium hydroxide, and when the mother liquor, wherein the calcium ions are eliminated, is neutralized, the mother liquor is suitable as a carbon source of a fermentation of glutamic acid or lysine. In spite of the reduction in carbon source purity, the yields of a glutamic acid and lysine are not reduced. We have further found that the yields of the said amino acids from fructose are far less than the same from glucose which is an indication that the production of glutamic acid and lysine is not dependent upon the presence of fructose.

DETAILED DESCRIPTION OF THE PREFERRED EMBODIMENTS

Molasses applicable to the present invention include cane molasses and beet molasses.

Hydrolysis of sucrose in the molasses may be carried out by known methods, such as by the use of mineral acid or an enzyme. For example, if the pH of molasses is adjusted to 1.5 - 2 with hydrochloric acid and is heated to 60° - 100° C for 0.5 - 4 hours, most of the sucrose in the molasses may be hydrolyzed to hexose, i.e., glucose and fructose.

When molasses is hydrolyzed with mineral acid, the hydrolyzate is neutralized with an alkali, such as calcium hydroxide or sodium hydroxide. Then, the neutral hydrolyzate is mixed with calcium hydroxide, preferably in an amount of 0.7 - 1.5 times the molar quantity of the hexose. Instead of calcium hydroxide, calcium oxide may be employed. In this instance, calcium oxide is first converted to calcium hydroxide in the hydrolyzate, and then reacted with fructose.

The mixing must be carried out cautiously. First, the neutral hydrolyzate is cooled to below 10° C, preferably below 5° C, and calcium hydroxide, in an amount of 1.2 - 1.6 times the molar quantity of the fructose, is added to the cold hydrolyzate. Then, the seed adducts of fructose and calcium hydroxide are preferably added, and the seeded mixture is aged for 15 - 60 minutes with moderate stirring. The adduct crystals may also crystallize without seeding. The remaining calcium hydroxide, is added gradually over a period of about 1 - 2 hours. During the reaction of calcium hydroxide with fructose, the temperature of the reactant is preferably kept below 5° C in order to decrease the decomposition of fructose and glucose. The above procedure produces large crystals of the adduct which are especially suitable for separation on an industrial scale.

Unless the mixing is carried out with caution, the resulting slurry will be creamy and will consist of mainly fine crystals. Accordingly, separation of crystals on an industrial scale will be difficult.

If the neutral hydrolyzate is mixed with calcium chloride instead of calcium hydroxide, the adduct crystals cannot be separated because the crystals precipitated will be fine and the slurry will be highly viscous.

The crystals so produced are recovered by filtering or centrifuging. The recovered crystals are preferably washed with chilled water.

Fructose crystals or a fructose solution containing small amount of glucose, can be prepared from the recovered crystals by known methods. The most preferable neutralizing agent for calcium hydroxide in the adduct is carbon dioxide. In this case, the crystals are placed into water, and then carbon dioxide gas is bubbled into the suspension. After the bubbling, the precipitate is removed thereby providing the crude fructose solution. The fructose solution can, if desired, further be purified by known methods, such as crystallization, ion exchange resin methods, and decolorization to prepare the final fructose crystals.

The yield of fructose from the hydrolyzate in the above solution may be as high as 70%, usually 60 - 65%.

The mother liquor is neutralized, and calcium ions are rmeoved from the liquor. Suitable neutralizing agents include carbon dioxide, sulfuric acid, phosphoric acid, cation exchange resins, or the like. When the neutralization is carried out by use of one of said exemplified agents, calcium ions can be removed simultaneously. Among the above agents, carbon dioxide is the most preferable, because recovered calcium carbonate can be used again by calcination. The other superiority of carbon dioxide is decolorization effect during neutralization.

Since both fructose and glucose are not stable in alkali solution, it is necessary that fructose and glucose are kept cold throughout the above procedure. It is also necessary that after fructose adduct is separated, both the adduct and the mother liquid is quickly neutralized.

The calcium-eliminated mother liquid is suitable for carbon source for glutamic acid and lysine. Most of the strains suitable for glutamic acid fermentation are also suitable for lysine fermentation.

The microognanic strains applicable to the present invention are the strains belonging to genus Brevibacterium, Corynebacterium, Micrococcus or Microbacterium and capable of producing glutamic acid or lysine. They include:

| Glutamic acid fermentation | |
|---|---|
| Brevibacterium lactofermentum | ATCC 13869 |
| B. divaricatum | NRRL-B-2311 |
| Corynebacterium glutamicum | ATCC 21543 |
| C. lilium | NRRL-B-22-43 |
| C. herculis | ATCC 13868 |
| Micrococcus glutamicus | ATCC 13032 |
| Microbacterium ammoniaphilum | ATCC 15354 |
| Lysine fermentation | |
| Brevibacterium lactofermentum | FERM-P 2654 |
| Corynebacterium glutamicum | ATCC 21543 |
| C. acetoglutamicum | FERM-P 2655 |
| Micrococcus glutamicus | ATCC 13286 |

Microorganisms identified by FERM-P numbers are available to the public from the Fermentation Research Institute, Agency of Industrial Science and Technology of the Ministry for Industrial Trade and Industry, Japan.

Fermentation is carried out according to the conventional manner in which molasses is employed as the main carbon source.

In spite of reduced carbon purity of the molasses due to the extraction of fructose, the fermentation yields are not reduced. As can be seen in Experiments 1 and 2, this superiority is supported by the fact that the fermentation yields in the case of glucose are higher than those in the case of fructose. Thus, it can be seen that the present invention takes advantage of both glucose in fermentation as well as the desirable fructose sweetness.

Having generally described the invention, a more complete understanding can be obtained by reference to certain specific examples, which are included for purposes of illustration only and are not intended to be limiting unless otherwise specified.

EXPERIMENT 1

Glutamic Acid Fermentation

Five batch experiments, wherein the fructose/glucose ratio was varied were performed. Each 20 ml culture medium containing:

| Hexose (described in Table 1) | 10 | g/dl |
|---|---|---|
| $KH_2PO_4$ | 0.1 | g/dl |
| $MgSO_4 \cdot 7H_2O$ | 0.05 | g/dl |
| $FeSO_4 \cdot 7H_2O$ | 0.001 | g/dl |
| $MnSO_4 \cdot 4H_2O$ | 0.001 | g/dl |
| $VB_1$ | 200 | γ/l |
| Biotin | 3 | γ/l |
| Soybean flake hydrolyzate (nitrogen content 7 g/dl) | 0.2 | ml/dl |
| pH 7.0 | | | was prepared, introduced into a 500 ml shaking flask, and sterilized at 110° C for 10 minutes.

Each medium was inoculated with Brevibacterium lactofermentum ATCC 13869, and cultured at 31.5° C for 40 hours with shaking. During the culturing, the pH of the medium was controlled between 7.0 and 8.0 with 45 g/dl sterilized aqueous urea solution. The results are shown in Table 1.

TABLE 1

| Hexose | | Bacterial | Glutamic | |
|---|---|---|---|---|
| Fructose (g/dl) | Glucose (g/dl) | Growth O.D. | Acid (g/dl) | Yield (%) |
| 10 | — | 0.30 | 2.43 | 24.3 |
| 7.5 | 2.5 | 0.38 | 2.77 | 27.7 |
| 5.0 | 5.0 | 0.47 | 3.38 | 33.8 |
| 2.5 | 7.5 | 0.49 | 4.91 | 49.1 |

TABLE 1-continued

| Hexose | | Bacterial | Glutamic | |
|---|---|---|---|---|
| Fructose (g/dl) | Glucose (g/dl) | Growth O.D. | Acid (g/dl) | Yield (%) |
| — | 10 | 0.50 | 4.86 | 48.6 |

EXPERIMENT 2

Five batch experiments were performed, each 20 ml culture medium containing:

| Hexose (described in Table 2) | 10 | g/dl |
|---|---|---|
| $(NH_4)_2SO_4$ | 4.5 | g/dl |
| $KH_2PO_4$ | 0.1 | g/dl |
| $MgSO_4 \cdot 7H_2O$ | 0.04 | g/dl |
| $FeSO_4 \cdot 7H_2O$ | 0.001 | g/dl |
| $MnSO_4 \cdot 4H_2O$ | 0.001 | g/dl |
| $VB_1$ | 200 | γ/l |
| Biotin | 50 | γ/l |
| Soybean flake hydrolyzate (nitrogen content 7 g/dl) | 1.5 | ml/dl |
| $CaCO_3$ | 5 | g/dl |
| pH 7.0 | | | was prepared, introduced into a 500 ml shaking flask, and sterilized at 110° C for 10 minutes.

Each medium was inoculated with Brevibacterium lactofermentum AJ 3796 (FERM-P 2654), and cultured at 31.5° C for 72 hours with shaking. The results are shown in Table 2.

TABLE 2

| Hexose | | Bacterial | | |
|---|---|---|---|---|
| Fructose (g/dl) | Glucose (g/dl) | Growth O.D. | L-Lys . HCl (g/dl) | Yield (%) |
| 10 | — | 1.15 | 1.81 | 18.1 |
| 7.5 | 2.5 | 1.16 | 2.13 | 21.3 |
| 5.0 | 5.0 | 1.14 | 2.34 | 23.4 |
| 2.5 | 7.5 | 1.04 | 3.59 | 35.9 |
| — | 10 | 1.03 | 3.62 | 36.2 |

EXAMPLE 1

Cane molasses was diluted with 2.3 l water per kg cane molasses, adjusted to pH 1.5 with sulfuric acid, and hydrolyzed at 60° C for 4 hours. The hydrolyzate was neutralized with calcium hydroxide, and precipitates of calcium sulfate were filtered out. Accordingly, invert sugar solution containing 9.95 g/dl glucose and 11.25 g/dl fructose was prepared.

Three liters of the invert sugar solution was cooled to 0° C and 30% calcium hydroxide containing 262 g Ca(OH)$_2$ (equal mole to hexose) was gradually added to the solution so that the temperature was kept below 5° C. When 70% amount of total calcium hydroxide was added, the addition was stopped and a small amount of the adduct crystals were seeded. For decreasing the supersaturation, the seeded solution was stirred for 30 minutes. During stirring, many adduct crystals crystallized out. The remaining 30% amount of calcium hydroxide was then gradually added for one hour, and the slurry so produced was further stirred for 30 minutes. The adduct crystals were filtered off, and washed with chilled water.

The recovered crystals were suspended into chilled water, the suspension was neutralized with sulfuric acid, and the precipitate formed was removed. The fructose solution so produced contained 168 g fructose and 6.4 g glucose. The yield of fructose was 50%.

The mother liquor was also neutralized with sulfuric acid, and the precipitate was removed. The calcium-eliminated mother liquor contained 284 g glucose and 159 g fructose.

In a comparison test, 1 kg of the same cane molasses was diluted with 1 liter of water, adjusted to pH 1.5 with sulfuric acid, and hydrolyzed at 60° C for 3 hours. 250 g Calcium chloride dihydrate was dissolved in 250 ml of water, and added to the hydrolyzate. The resulting solution was concentrated to crystallize the adduct of fructose and calcium chloride. However, the adduct crystals so produced could scarcely be separated because of the high viscosity of the slurry and the fineness of the crystal size.

Six batches of glutamic acid fermentation test were carried out using the cane molasses, the invert sugar solution for calcium hydroxide and the concentrated calcium-eliminated mother liquor (containing 23.16% glucose and 12.97% fructose) as the main carbon source.

Each 20 ml culture medium contained:

| | | |
|---|---|---|
| One of the above main carbon sources | 100 | g/l (as hexose) |
| $KH_2PO_4$ | 1 | g/l (as hexose) |
| $MgSO_4 \cdot 7H_2O$ | 1 | g/l (as hexose) |
| $VB_1$ | 100 | γ/l |
| Soybean flake hydrolyzate (nitrogen content 70 g/l) pH 7.0 | 4 | ml/l | was prepared, placed in a 500 ml shaking flask, and sterilized at 115° C for 10 minutes.

The medium was inoculated with Brevibacterium lactofermentum ATCC 13869 and cultured at 31.5° C for 40 hours with shaking. In order that pH of the medium is kept between 6.5 and 8.0, 450 g/l aqueous urea solution was sometimes added.

After the inoculation, when optical density of 26 times diluted solution of the culture broth at 562 nm reached 0.3, a surface-active agent mainly consisting of polyoxyethylenesorbitan monopalmitate was added to the broth in concentration of 3 mg/ml.

The yields of glutamic acid were 48.2 g/l to the cane molasses, 47.9 g/l to the invert sugar solution and 48.1 g/l to the calcium-eliminated mother liquor, respectively.

Using the same carbon sources as above in which the invert sugar solution was omitted, the glutamic acid fermentation tests were carried out as to other six microrganic strains. The fermentation procedure was the same as the case of B.lactofermentum, except that the concentration of Vitamin $B_1$ was 200 γ/l, soybean flake hydrolyzate was not added, and the culturing period was 30 hours.

The strains employed in the tests and the yields of glutamic acid were as shown in Table 3.

TABLE 3

| | Yield | |
|---|---|---|
| Strain | Cane molasses | Ca-eliminated mother liquor |
| Corynebacterium lilum (NRRL-B-22-43) | 48.3 | 49.0 |
| Corynebacterium herculis (ATCC 13868) | 45.2 | 46.5 |
| Brevibacterium divaricatum (NRRL-B-2311) | 46.6 | 47.2 |
| Micrococcus glutamicus (ATCC 13032) | 48.5 | 49.3 |
| Microbacterium ammoniaphilum (ATCC 15354) | 48.3 | 49.0 |
| Brevibacterium lactofermentum (ATCC 13869) | 52.1 | 52.9 |

EXAMPLE 2

Using the same carbon sources as employed in Example 1, lysine fermentation tests were carried out.

Each 20 ml culture medium contained:

| | | |
|---|---|---|
| One of the above main carbon sources | 100 | g/l (as hexose) |
| $(NH_4)_2SO_4$ | 45 | g/l (as hexose) |
| $KH_2PO_4$ | 1 | g/l (as hexose) |
| $MgSO_4 \cdot 7H_2O$ | 0.4 | g/l (as hexose) |
| $FeSO_4 \cdot 7H_2O$ | 0.01 | g/l (as hexose) |
| $MnSO_4 \cdot 4H_2O$ | 0.01 | g/l (as hexose) |
| $VB_1$ | 200 | γ/l |
| Biotin | 50 | γ/l |
| Soybean flake hydrolyzate (nitrogen content 70 g/l) | 15 | ml/l |
| Calcium carbonate pH 7.0 | 50 | g/l | was prepared, placed in 500 ml shaking flask, and sterilized at 115° C for 10 minutes.

Each medium was inoculated with Brevibacterium lactofermentum FERM-P 2654 or Corynebacterium acetoglutamicum FERM-P 2655, and cultured at 30.5° C for 72 hours with shaking. After the culturing, the lysine concentration of the broth was determined and shown in Table 4.

TABLE 4

| | L-Lys HCl | |
|---|---|---|
| Carbon Source | B. lactofermentum FERM-P 2654 | C. acetoglutamicum FERM-P 2655 |
| Cane molasses | 40.7 g/l | 29.2 g/l |
| Invert sugar solution | 38.5 | 26.9 |
| Ca-eliminated mother liquor | 41.2 | 30.3 |

Using the same carbon sources as above, in which the invert sugar solution was omitted, the lysine fermentation tests were carried out as to the other two strains. The fermentation procedure was the same as the case of B.lactofermentum and C.acetoglutamicum, except that the concentration of soybean flake hydrolyzate was 10 ml/l, pH of the medium was 8.0 and the cultivation temperature was 31.5° C.

The strains employed in the tests and the yields of lysine are shown in Table 5.

TABLE 5

| | Yield | |
|---|---|---|
| Strain | Cane molasses | Ca-eliminated mother liquor |
| Micrococcus glutamicus (ATCC 13286) | 30.5% | 30.9% |
| Corynebacterium glutamicum (ATCC 21543) | 30.1 | 30.5 |

EXAMPLE 3

Beet molasses was diluted with 2.5 l water per kg beet molasses, adjusted to pH 1.5 with sulfuric acid, and hydrolyzed at 60° C for 4 hours. The hydrolyzate was neutralized with calcium hydroxide, the precipitates formed were filtered out. Accordingly, invert sugar solution containing 7.80 g/dl glucose and 8.81 g/dl fructose was prepared.

Three liters of the invert sugar solution was cooled to 0° C and 30% calcium hydroxide containing 205 g Ca(OH)$_2$ (equal mole to hexose) was gradually added to the solution so that the temperature was kept below 5° C. When 70% the amount of total calcium hydroxide was added, the addition was stopped and a small amount of the adduct crystals were seeded. For decreasing the supersaturation, the seeded solution was stirred for 30 minutes. During stirring, many adduct crystals crystallized out. The remaining 30% amount of calcium hydroxide was then gradually added for one hour, and the slurry so produced was further stirred for 30 minutes. The adduct crystals were filtered off, and washed with chilled water.

The recovered crystals were suspended into chilled water, the suspension was neutralized with sulfuric acid, and the precipitate formed was removed. The fructose solution so produced contained 169 g fructose (Yield: 64%) and 6.3 g glucose.

As to the mother liquor, it was also neutralized with sulfuric acid, and the precipitate was removed. The calcium-eliminated mother liquor contained 220 g glucose and 87 g fructose.

Twelve batches of glutamic acid fermentation test were carried out using the beet molasses and the concentrated calcium-eliminated mother liquor as a main carbon source.

Each 20 ml culture medium contained:

| | | |
|---|---|---|
| One of the above main carbon source | 100 | g/l (as hexose) |
| Soybean flake hydrolyzate ("Mieki" nitrogen content 2.4%) | 10 | ml/l |
| pH 7.0 | | | was prepared, placed in a 500 ml shaking flask, and sterilized at 115° C for 10 minutes.

The medium was inoculated with one of the strains described in Table 6, and cultured at 31.5° C for 30 hours with shaking. In order that pH of the medium is kept between 6.5 and 8.0, 400 g/l aqueous urea solution was sometimes added.

After inoculation, when optical density of 26 times diluted solution of the culture broth at 562 nm reached 0.3, a surface active agent mainly consisting of polyoxyethylenesorbitan monopalmitate was added to the broth in concentration of 0.4 mg/ml.

The strains employed in the tests and the yields of glutamic acid were shown in Table 6.

TABLE 6

| | Yield | |
|---|---|---|
| Strain | Beet molasses | Ca-eliminated mother liquor |
| Corynebacteriu lilium (NRRL-B-22-43) | 54.2% | 55.0% |
| Corynebacterium herculis (ATTC 13868) | 50.3 | 52.0 |
| Brevibacterium divaricatum (MRRL-B-2311) | 52.4 | 52.9 |
| Micrococcus glutamicus (ATCC 13032) | 54.4 | 55.1 |
| Microbacterium ammoniaphilum (ATCC 15354) | 54.3 | 55.0 |
| Brevibacterium lactofermentum (ATCC 13869) | 58.4 | 59.8 |

EXAMPLE 4

Using the same carbon sources as employed in Example 3, lysine fermentation were carried out.

Each 20 ml culture medium contained:

| | | |
|---|---|---|
| One of the above main carbon sources | 100 | g/l (as hexose) |
| (NH$_4$)$_2$SO$_4$ | 45 | g/l (as hexose) |
| KH$_2$PO$_4$ | 1 | g/l (as hexose) |
| MgSO$_4$ . 7H$_2$O | 0.4 | g/l (as hexose) |
| VB$_1$ | 200 | γ/l |
| Biotin | 500 | γ/l |
| Soybean flake hydrolyzate (nitrogen content 70 g/l) | 15 | ml/l |
| Calcium carbonate | 50 | g/l |
| pH 7.0 | | | was prepared, placed in 500 ml shaking flask, and sterilized at 115° C for 10 minutes.

Each medium was inoculated with Brevibacterium lactofermentum FERM-P 2654 and cultured at 33° C for 72 hours with shaking.

The yields of lysine were 46.2 g/dl to the beet molasses and 46.5 g/dl to the calcium-eliminated mother liquor, respectively.

Using the same carbon sources as above, the lysine fermentation tests were carried out as to the other two strains. The fermentation procedure was the same as the case of B.lactofermentum, except for the following points.

As to the culture medium, 0.01 g/l FeSO$_4$.7H$_2$O and 0.01 g/l MnSO$_4$.4H$_2$O were newly added, the concentration of Biotin and soybean flake hydrolyzate were changed to 50 γ/l and 10 ml/l, respectively, and the pH of the medium was 8.0. As to the culturing, the temperature was maintained at 31.5° C.

The strains employed in the tests and the yields of lysine were shown as in Table 7.

TABLE 7

| | Yield | |
|---|---|---|
| Strain | Beet Molasses | Ca-eliminated mother liquor |
| Micrococcus glutamicus (ATCC 13286) | 30.2% | 30.8% |
| Corynebacterium glutamicum (ATCC 21543) | 30.0 | 30.7 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In the fermentation production of glutamic acid or lysine wherein fermentation is effected by the use of a microorganism of the genus Brevibacterium, Corynebacterium, Micrococcus or Microbacterium, the improvement which comprises:
    admixing a substantially neutral hydrolyzate of molasses containing glucose and fructose cooled to below 10° C with calcium hydroxide to form a fructose addition product precipitate, and
    neutralizing the remaining mother liquor, simultaneously eliminating calcium ions therefrom, and utilizing the remaining liquor as the carbon source for said fermentation.

2. The method of claim 1, wherein the pH of the molasses is adjusted to 1.5 – 2 and thereafter hydrolyzed at a temperature of 60° – 100° C for 0.5 to 4 hours.

3. The method of claim 2, wherein the hydrolyzed molasses is neutralized with an alkali and thereafter calcium hydroxide is added thereto to precipitate the fructose addition product.

4. The method of claim 3, wherein neutralizing the mother liquor and simultaneously eliminating calcium ions is accomplished by introducing carbon dioxide gas and precipitation of calcium carbonate.

5. The method of claim 3, wherein neutralizing the mother liquor and simultaneously eliminating calcium ions is accomplished by the addition of sulfuric acid.

* * * * *